United States Patent [19]

Trescony et al.

[11] Patent Number: 5,607,464
[45] Date of Patent: Mar. 4, 1997

[54] PROSTHETIC VASCULAR GRAFT WITH A PLEATED STRUCTURE

[75] Inventors: Paul V. Trescony, Robbinsdale; Michael Wolf, Brooklyn Park; Richard Molacek, Maple Grove; Elaine Lindell, Blaine, all of Minn.

[73] Assignee: Medtronic, Inc., Minneapolis, Minn.

[21] Appl. No.: 113,542

[22] Filed: Aug. 27, 1993

Related U.S. Application Data

[62] Division of Ser. No. 914,648, Jul. 15, 1992, Pat. No. 5,282,847, which is a continuation of Ser. No. 662,667, Feb. 28, 1991, abandoned.

[51] Int. Cl.⁶ .................................. A61F 2/06; A61F 2/04
[52] U.S. Cl. ..................................................... 623/1; 623/12
[58] Field of Search .................................. 623/1, 11, 12; 600/36; 606/194

[56] References Cited

U.S. PATENT DOCUMENTS

| | | |
|---|---|---|
| 3,479,670 | 11/1969 | Medell . |
| 3,657,744 | 4/1972 | Ersek ........................ 623/12 |
| 3,986,288 | 10/1976 | Hoffman . |
| 4,140,126 | 2/1979 | Choudhury .................. 623/1 |
| 4,300,244 | 11/1981 | Bokros . |
| 4,313,231 | 2/1982 | Koyamada ................... 623/1 |
| 4,550,447 | 11/1985 | Seiler, Jr. . |
| 4,605,406 | 8/1986 | Cahalan . |
| 4,629,458 | 12/1986 | Pinchuk . |
| 4,647,416 | 3/1987 | Sieler, Jr. . |
| 4,759,757 | 7/1988 | Pinchuk . |
| 4,770,664 | 9/1988 | Gogolewski . |
| 4,834,736 | 5/1989 | Kira ........................... 623/1 |
| 4,834,746 | 5/1989 | Kira . |
| 4,892,539 | 1/1990 | Koch . |
| 4,941,870 | 7/1990 | Okada . |

FOREIGN PATENT DOCUMENTS

| | | |
|---|---|---|
| 0256748 | 2/1988 | European Pat. Off. . |
| 2187463 | 9/1987 | United Kingdom . |
| 2199327 | 7/1988 | United Kingdom . |
| 8303349 | 10/1983 | WIPO . |

OTHER PUBLICATIONS

Journal of Vascular Surgery, vol. 15, No. 1, pp. 176–186, Jan. 1992, *Myointimal Thickening in Experimental Vein Grafts is Dependent on Wall Tension* by Lewis B. Swartz, M. D. et al.
Bio–Medical Materials and Engineering, vol. 2, pp. 171–183, 1992, *Flow Vissualization Analysis in a Model of Artery–Graft Anastomosis* by Takeo Matsumoto et al.
Journal of Vascular Surgery, vol. 13, No. 5, pp. 738–740, May 1991, *Special Communication* by James C. Stanley, M. D. and Christopher K. Zarins, M. D.
ASAIO Journal 1993, pp. M501–M505, *An in Vitro Endothelialized Compliant Vascular Graft Minimizes Anastomotic Hyperplasia* by Hiromichi Miwa et al.
"Elastic Properties and Strength of a Novel Small–Diameter, Compliant Polyurethane Vascular Graft", J. Biomed.Matrl-.Red: Applied Biomaerials 23 (1989) pp. 229–244.
CV MIS Profile #10 (1987).
ARTERY, Bauman et al., pp. 67–99 (1978).
"The Internal Elastic Membrane and Intimal Folds in Arteries: Important but Neglected Structures", Svendsen et al., Acta Physiological Scandinava, Supp. 572 (1988).
"Enhanced Production of an Endothelium–Derived Contracting Factor by Endothelial Cells Subjected to Pulsatile Stretch", SURGERY by Sumpio et al., Aug., 1990, pp. 277–282.
"The Challenge of Small Diameter Vascular Grafts", Medical Progress Through Technical, by Burkel, 14 (1988) pp. 165–175.

*Primary Examiner*—Debra S. Brittingham
*Attorney, Agent, or Firm*—Daniel W. Latham; Harold R. Patton

[57] ABSTRACT

A vascular graft having a pleated circumference accommodates blood pressure changes with minimal change in internal surface area. A highly compliant graft may be made from a wide variety of polymers including non-elastomeric materials.

14 Claims, 2 Drawing Sheets

PROSTHETIC VASCULAR GRAFT WITH A PLEATED STRUCTURE

This is a divisional of application(s) Ser. No. 07/914,648 filed on Jul. 15, 1992 now U.S. Pat. No. 5,282,847, which is a continuation of Ser. No. 07/662,667 filed on Feb. 28, 1991, now abandoned.

FIELD OF THE INVENTION

This invention is directed to synthetic vascular grafts.

BACKGROUND OF THE INVENTION

Vascular grafts are currently used to augment or replace certain diseased arteries. Operations for this purpose are commonly done by surgeons who attach the graft to the side of the vessel proximal to the diseased region and again to the side of the vessel distal to the diseased region, thus bypassing the diseased region. Alternatively the graft is joined to the ends of the vessel remaining after removing the diseased portion. Clinically used artificial grafts have generally been restricted to vessel replacements requiring grafts of 6 mm and larger diameter, e.g., abdominal aorta, and lilac, femoral, and popliteal arteries. Natural vessels taken from other parts of the patients body, e.g., saphenous vein in the leg or internal mammary artery, are with few exceptions the choice for less than 6 mm diameter applications. Examples of the clinically used artificial vessels for arteries of large diameter are, for instance, DeBakey artificial vessel made of woven Dacron® (trademark of DuPont) and Gore-Tex® (Gore Co., Ltd., U.S.A.) which is made of expanded polytetrafluoroethylene (hereinafter "EPTFE").

According to U.S. Pat. No. 4,834,746 the prior Dacron® and EPTFE graft materials have proven unsuitable at diameters of less than about 6 mm because of the compliance mismatch between the natural and artificial vessels. The proposed solution in U.S. Pat. No. 4,834,746 is to produce a vessel made of a microporous elastomer material. Elastomeric materials, however, lose wall thickness in the process of expansion and therefore eventually can result in aneurysm. Thus a conventional circular perimeter graft which merely utilizes an elastomeric material to provide a compliance match is not considered a fully satisfactory design.

Other variations in materials and configurations for vascular grafts are known, for example from U.S. Pat. Nos. 4,892,539; 4,605,406; 4,941,870; 4,759,757; 4,629,458; 4,300,224; and 4,647,416 as well as GB 2187463 and EP 0256748.

However, there still exists a need for improved vascular graft structure, particularly for graft structures which can be used at diameters below 6 mm.

SUMMARY OF THE INVENTION

The invention provides a novel artificial tubular graft structure characterized by a pleated circumference. The new graft provides a structure with high compliance, resistance to aneurysm and a luminal surface area which remains substantially unchanged during expansion.

There may also be a connection between stretching of the surface on which endothelial cells are resting and blockage (stenosis) of the vessel wall due to underlying smooth muscle cell proliferation (hyperplasia). An additional factor promoting stenosis through smooth muscle cell hyperplasia may be the attachment of a non-compliant tube (the usual synthetic graft) to the compliant artery. Chronic flexing at the anastomosis and/or flow disturbances may result from this attachment, both of which could contribute to hyperplasia. If any of these connections are made in vivo, the inventive graft design, providing a compliant structure while minimizing wall stretch during cyclic pulsatile expansion, will prove even more desirable.

Although the novel graft structure may be made of conventional materials (e.g. knitted or woven fabrics and EPTFE), solid wall constructions made from polymers which are relatively stiff compared to prior art materials can also be used.

The inventive structures have good inherent kink resistance. Whereas conventional tubular grafts tend to develop a kink when bent around a tight radius, the pleated tube of the invention tends to fold flat when bent around a tight radius because pleats at opposite sides form natural seams allowing the tube to lay flat rather than kink.

In an alternative embodiment at least some of the longitudinal pleats have a wave-like or corrugated configuration in the longitudinal direction. Preferably such longitudinally corrugated pleats are regularly spaced around the circumference between sections of straight pleats to provide the graft with even greater kink resistance. Additional kink resistance may alternatively be provided by providing the pleats with a twist about the longitudinal axis.

DETAILED DESCRIPTION OF THE INVENTION

Figure 1:
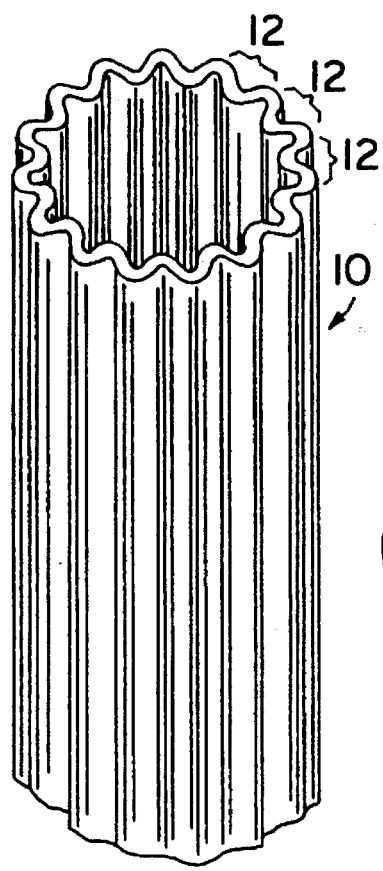
FIG. 1 is a fragmentary perspective view of the one embodiment of the vascular graft of the invention.

In FIG. 1 there is shown an embodiment of the vascular graft of the invention in its simplest form. The graft 10 has a pleated circumference, the individual pleats 12 extending longitudinally along and parallel to the central axis of the tube.

The term "apparent diameter" when used herein to describe a pleated vessel of the invention refers to the diameter of a circle circumscribing the outer pleat tips.

Figure 2:
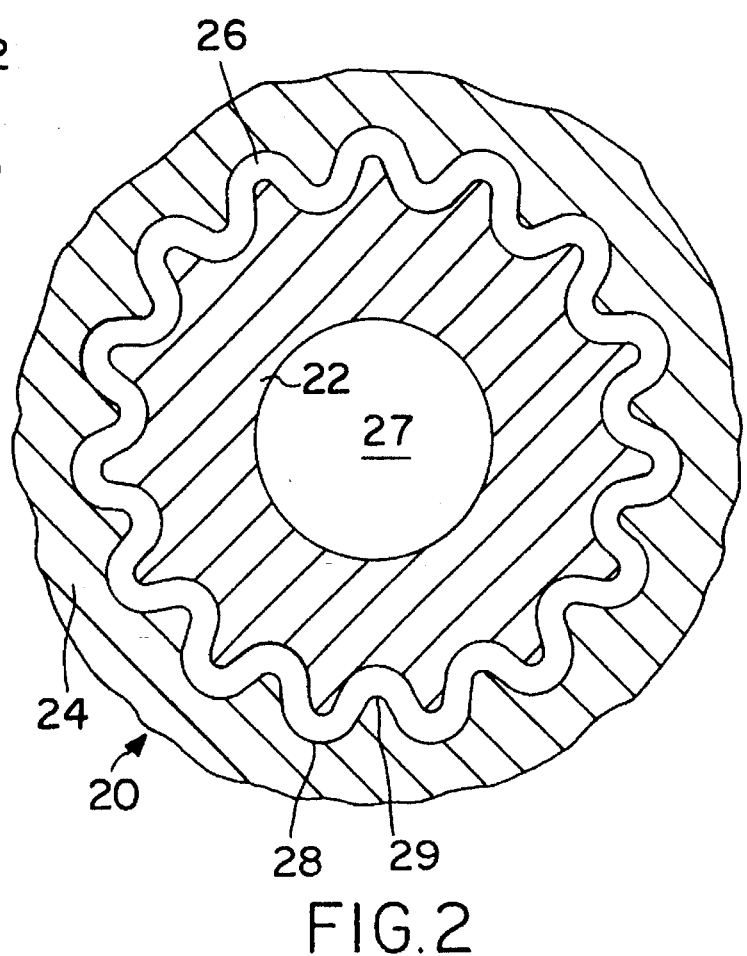
FIG. 2 is a fragmentary cross-section taken across the axis of an extrusion die used to form the graft of FIG. 1.

The graft may suitably be formed by extrusion from a die 20 as shown in FIG. 2, followed by a drawing down of the extruded tube to reduce its diameter and waft thickness. The die 20 comprises a toothed core 22 and a mating jacket 24 separated by an extrusion gap 26. A central hole 27 in core 22 allows for inflation of the extruded tube with air or other suitable fluid during draw down to prevent collapse of the tubular structure. An extrusion die as shown in FIG. 2 having 15 teeth about its circumference, an apparent diameter of 8.15 mm, an extrusion gap 26 of 0.38 mm, and a pleat depth (tip 28 to valley 29) of 0.69 mm has been found to produce acceptable 7 mm or smaller apparent diameter graft materials with several polymers such as Kraton™ G2075, a thermoplastic rubber sold by Shell Oil Co., Pellathane™ 2363-80A a polyurethane sold by Dow Chemical Co., and C-Flex™ R70-001 EM50A, a styrene olefin copolymer sold by the Concept Polymer Technology Inc. Blends of resins, such as 5–25% polypropylene with Kraton G2075 or C-Flex™, or 1–5% K-Resin™ KR03, a styrenebutadiene copolymer sold by Phillips 66 Co., with C-Flex™ have also been successfully employed. The C-Flex™ extrusions may readily be drawn down to apparent diameters of 3 mm without tearing or loss of pleated profile.

Figure 3:
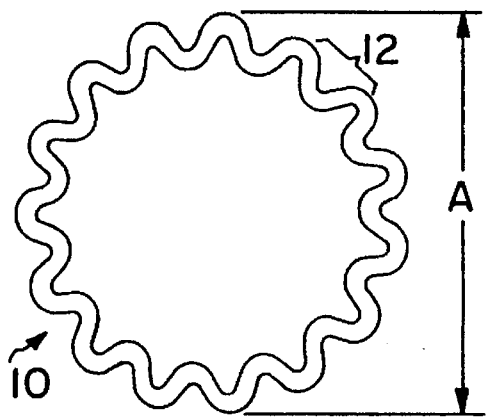
FIG. 3 is a sectional view showing a preferred form of the invention inflated at the lowest normal physiological pressure.
Figure 4:
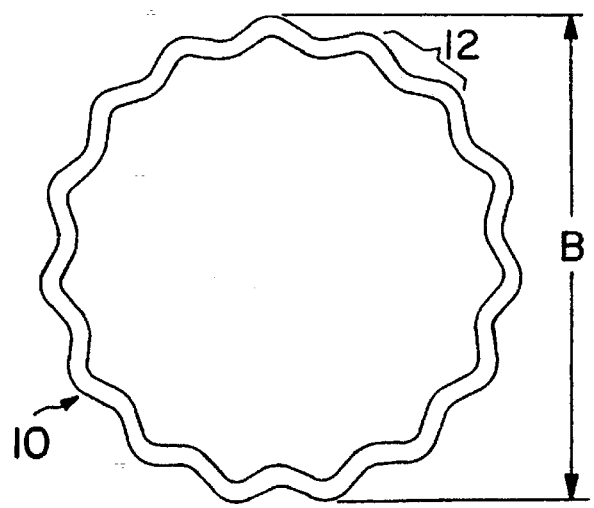
FIG. 4 is a sectional view of the graft of FIG. 3 shown when subjected to the highest normal physiological pressure.

FIGS. 3 and 4 are sectional views of a preferred graft 10 shown as it appears when subjected to normal physiological blood pressures. As shown in FIG. 3, graft 10, having an apparent diameter A, is pleated and sized to maintain its fully relaxed pleated form at the lowest normal blood pressure. At the highest pressure, the cross-sectional area is substantially increased due to unfolding of the pleats 12, providing the graft with a new larger apparent diameter B. Preferably the graft 10 remains slightly pleated at highest normal blood pressure, as shown in FIG. 4, so that the enlargement in cross-sectional area produces little or no change in wall perimeter dimension. Thus, under normal conditions there is little or no tensile stress on the graft wall due to normal pulsing blood flow therethrough. To achieve this property those skilled in the art will appreciate that the polymer selected and the graft wall thickness may be varied to provide a suitable flexural response to the blood pressure change while the number and depth of the pleats may be varied to provide the desired volume differential between the relaxed and the fully expanded forms of the graft.

With the invention polymers of high tensile strength can be used since normal pressure differentials are accommodated in the flexural mode by unfolding of the pleats. Because most materials have a lower flexural modulus than tensile modulus, many materials that have good biocompatibility but were too stiff to use in prior vascular graft configurations can now be used in the inventive pleated structure.

Typical wall thicknesses range from 0.01" or less, suitably between 0.002" and about 0.007". Desirably the number of pleats about the circumference is at least 8, more preferably at least 15. Suitable expansion ratios (i.e. increased cross-sectional areas of the graft between lowest and highest normal physiciogical pressures) are at least 5%, preferably at least 25%, more preferably 40% or more.

For relatively stiff polymers, such as solid polypropylene or polytetrafluoroethylene, it is preferable to utilize a plurality of nested thin walled tubes, desirably about 0.025 mm or less thick, optionally encasing a reinforcing layer, to produce a graft with good drape during handling and good suturability.

While the graft may be made from of a highly elastomeric polymer so that the circumference is expandable beyond the fully unfolded circumference, it is most preferred that the material have a low flexural modulus but a relatively high tensile strength. This is considered desirable to increase the graft's resistance to aneurysm. If the pleated graft of the invention were to expand beyond its designed operating limits and the pleated structure was fully unfolded, the stress on the wall would be completely borne as a circumferential tensile stress. Because the tensile modulus is greater than the flexural modulus, expansion beyond the design limit would result in a radially stiffer graft, more resistant to aneurysm.

A further advantage of the invention is that the luminal surface area remains substantially unchanged during normal expansion. As long as the pleated structure remains, the wall circumference, and hence the luminal surface area, remains relatively unchanged during expansion of the graft. In vitro studies have shown that endothelial and smooth muscle cells (which line normal vessels and colonize graft materials, a process often encouraged by cell seeding prior to implementation) modify their biological activity in response to stretching. In particular, endothelial cells increase production of endothelin a potent peptide hormone vasoconstrictor and smooth muscle cell chemotractant. It is believed that with a pleated vascular graft of the invention endothelial cells adhered thereto will produce relatively less endothelial than when adhered to a non-pleated elastomeric graft, thereby lessening the tendency for hyperplasia to develop within or contiguous to the prosthetic graft.

A still further advantage of the invention is that a solid wall can be used. While the particular material chosen is not considered critical to the invention, so that porous, woven or knitted fabric, or EPTFE materials may be used, graft porosity at least on the internal surface of the graft may be considered disadvantageous because:

(a) hemostasis may require precoating or preclotting;

(b) tissue ingrowth may result in thrombus formation at the luminal wall surface;

(c) growth of an endothelial cell layer at the lummsl wall face may be inhibited by the roughness of a porous wall material; and (d) wall degradation may be increased by allowing ingrowth of inflammatory cells and an increased surface-to-volume ratio with porous materials.

Figure 5:
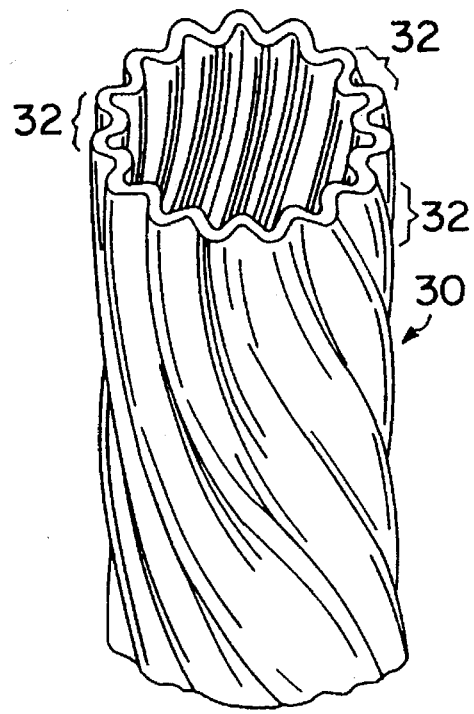
FIG. 5 is a fragmentary perspective view of an alternate embodiment of the invention in which the pleats are twisted along the axis of the graft to provide improved kink resistance.
Figure 6:
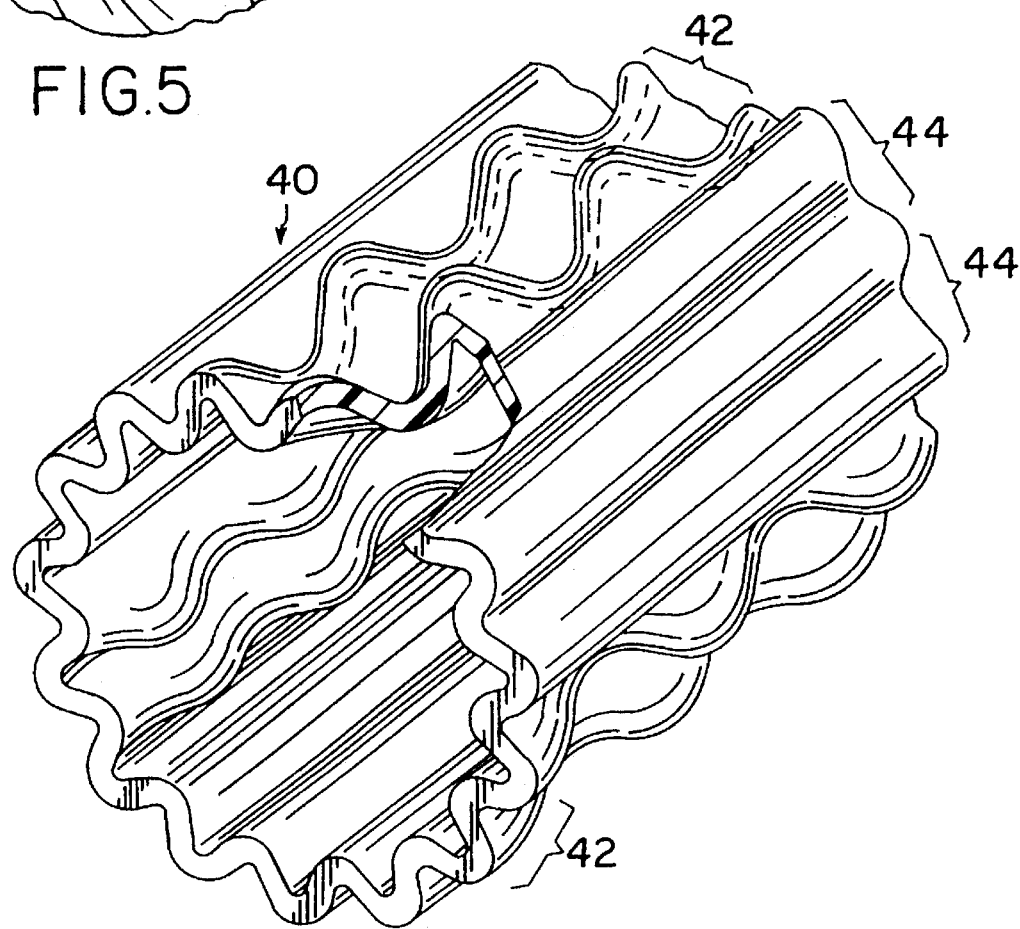
FIG. 6 is a fragmentary perspective view of a second alternate embodiment of the invention in which some of the pleats are corrugated for improved kink resistance.

The inventive grafts of FIG. 1 have some natural resistance to kinking, tending to flatten out but not completely close when sharply bent without internal pressurization. However, additional kink resistance can be incorporated into the graft of the invention as shown in FIGS. 5 and 6. In FIG. 5 a pleated graft 30 is shown having longitudinal pleats 32 which are twisted so that they spiral around the axis of the tube rather than running parallel thereto. In FIG. 6 a graft 40 is shown in which some of the pleats are corrugated to provide a wave-like pattern when viewed from the side. These corrugated pleats 42 may be uniformly distributed around the circumference of the graft between uncorrugated pleats 44. Suitably one or two corrugated pleats 42 are separated by a cluster of three or four uncorrugated pleats 44. Optionally all of the pleats may be corrugated. In alternative embodiments not shown, a side-to-side wavelike pattern for some or all of the pleats may be provided.

Another modification of the inventive structure which may be employed is to provide a multi-layered wall of different polymer materials. For instance, the internal wall may be a very thin layer of a polymer such as polystyrene which provides a good surface for endothelial cell growth while the outer layer may be of a porous material which allows the graft to be anchored in surrounding tissues. Such multi layered structures may be provided by co-extrusion, by internal or external coatings on a graft wall, or by other known techniques for providing laminated or nested polymer structures.

A multi-layered structure would allow very thin walls to be used with sufficient strength due to the multiple layers. A thin wall profile would also allow fabrication of the graft with more pleats in the wall and/or deeper pleats.

Those skilled in the art will appreciate that the grafts of the invention can be manufactured by many techniques. For instance, in addition to those already described, the grafts may be manufactured by precipitation from solution or emulsion, by vacuum forming thermoplastic or curing thermoset materials on a mandrel, or by solution extrusion into an appropriate bath where the solvent would be extracted to provide a reduced wall thickness graft. The techniques of U.S. Pat. Nos. 4,605,406, 4,834,746 and 4,770,664, the disclosures of which are incorporated herein by reference, may for instance be readily adapted to manufacture grafts of the invention from various polymer solutions. Other manufacturing techniques will be readily apparent to those skilled in the art.

The vascular graft of the present invention may be used in the same manner as a vascular graft of conventional design. For example, it may be cut to a desired length and sutured to a blood vessel at its ends according to conventional vascular graft techniques.

What is claimed is:

1. A method for treating an arterial blood vessel having a diseased portion comprising the steps of:
   (a) creating a first opening in a first portion of the blood vessel upstream of the diseased portion;
   (b) creating a second opening in a second portion of the blood vessel downstream of the diseased portion;
   (c) proving a vascular graft having a first end and a second end and a flexible, tubular wall structure with longitudinally extending pleats therebetween; and
   (d) compliantly securing the first and second ends of the vascular graft to the first and second openings, whereby blood flow through the vessel is provided by the pleated vascular graft.

2. The method of claim 1 wherein the tubular wall structure has at least 8 pleats.

3. The method of claim 1 wherein the tubular wall structure has an expansion factor of at least 25%.

4. The method of claim 1 wherein the vascular graft is made from a biocompatible polymer material selected from the group consisting of silicone polymers, polytetrafluoroethylene, polyesters, polystyrene, polyurethanes, styrene-olefin copolymers, styrene block copolymers, polyethylene, polypropylene and blends thereof.

5. The method of claim 1 wherein the vascular graft is secured to the blood vessel by suturing.

6. The method of claim 1 wherein the vascular graft bypasses the diseased portion.

7. The method of claim 1 wherein the vascular graft replaces the diseased portion.

8. A method for treating an arterial blood vessel having a diseased portion by the use of a vascular graft with a diameter of less than about 6 mm, the method comprising the steps of:
   (a) creating a first opening in a first portion of the blood vessel upstream of the diseased portion;
   (b) creating a second opening in a second portion of the blood vessel downstream of the diseased portion;
   (c) providing a vascular graft having a first end and a second end and a flexible, tubular wall structure with longitudinally extending pleats therebetween, said graft having a diameter of less than about 6 mm; and
   (d) compliantly securing the first and second ends of the vascular graft to the first and second openings such that blood may flow through the pleated vascular graft.

9. The method of claim 8 wherein the tubular wall structure has at least 8 pleats.

10. The method of claim 8 wherein the tubular wall structure has an expansion factor of at least 25%.

11. The method of claim 8 wherein the vascular graft is made from a biocompatible polymer material selected from the group consisting of silicone polymers, polytetrafluoroethylene, polyesters, polystyrene, polyurethanes, styrene-olefin copolymers, styrene block copolymers, polyethylene, polypropylene and blends thereof.

12. The method of claim 8 wherein the vascular graft is secured to the blood vessel by suturing.

13. The method of claim 8 wherein the vascular graft bypasses the diseased portion.

14. The method of claim 8 wherein the vascular graft replaces the diseased portion.

* * * * *